United States Patent [19]

Junino et al.

[11] Patent Number: 5,202,487
[45] Date of Patent: Apr. 13, 1993

[54] 2-SUBSTITUTED PARA-AMINOPHENOLS AND THEIR USE FOR DYEING KERATINOUS FIBRES

[75] Inventors: Alex Junino, Livry-Gargan; Gerard Lang, Saint-Gratien; Alain Genet, Aulnay-sous-Bois, all of France

[73] Assignee: L'Oreal, Paris, France

[21] Appl. No.: 933,583

[22] Filed: Aug. 24, 1992

Related U.S. Application Data

[60] Continuation of Ser. No. 645,404, Jan. 24, 1991, abandoned, which is a division of Ser. No. 633,190, Dec. 28, 1990, Pat. No. 5,053,052, which is a continuation of Ser. No. 406,269, Sep. 12, 1989, abandoned.

[30] Foreign Application Priority Data

Sep. 13, 1988 [FR] France .................................. 8811926

[51] Int. Cl.$^5$ ............................................. C07C 323/29
[52] U.S. Cl. ...................................... 564/443; 8/411; 8/412; 8/421; 564/440
[58] Field of Search ................ 564/443, 440; 8/411, 8/412, 421

[56] References Cited

U.S. PATENT DOCUMENTS

| | | | |
|---|---|---|---|
| 1,940,757 | 12/1933 | Lehmann et al. | 8/411 |
| 3,666,812 | 5/1972 | Kalopissis et al. | 564/443 |
| 3,712,927 | 1/1973 | Howe et al. | 430/211 |
| 4,588,410 | 5/1986 | Konrad et al. | 8/421 |
| 4,863,924 | 9/1989 | Hage et al. | 514/247 |
| 4,997,451 | 3/1991 | Clausen et al. | 8/421 |

FOREIGN PATENT DOCUMENTS

| | | |
|---|---|---|
| 0182187 | 5/1986 | European Pat. Off. . |
| 0226072 | 6/1987 | European Pat. Off. . |
| 331144 | 9/1989 | European Pat. Off. . |
| 048256 | 2/1980 | Japan . |
| 8602829 | 5/1986 | World Int. Prop. O. ............. 8/421 |

OTHER PUBLICATIONS

Chemical Abstracts, vol. 109, No. 15, Oct. 10, 1988, p. 649, No. 128609s.
Chemical Abstracts, vol. 98, No. 14, 1983, No. 110060a.

Primary Examiner—Allen J. Robinson
Assistant Examiner—Scott C. Rand
Attorney, Agent, or Firm—Jacobson, Price, Holman & Stern

[57] ABSTRACT

2-Substituted para-aminophenols of general formula:

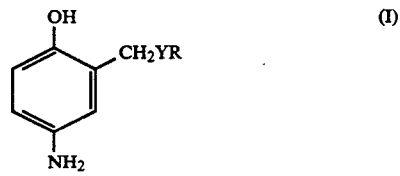

where Y denotes oxygen or sulphur and R denotes a $C_1$–$C_6$ alkyl, $C_1$–$C_6$ hydroxyalkyl or $C_1$–$C_6$ haloalkyl or a $C_2$–$C_6$ polyhydroxyalkyl, provided that when Y=O, R is not methyl or ethyl and when Y=S, R is not ethyl; and dye composition containing one or more compounds of formula (I) where Y denotes an oxygen or sulphur atom and R is $C_1$–$C_6$ alkyl, $C_1$–$C_6$ hydroxyalkyl, $C_1$–$C_6$ haloalkyl or $C_2$–$C_6$ polyhydroxyalkyl.

6 Claims, No Drawings

2-SUBSTITUTED PARA-AMINOPHENOLS AND THEIR USE FOR DYEING KERATINOUS FIBRES

This application is a continuation of application Ser. No. 07/645,404, filed Jan., 24, 1991, now abandoned which is a division of application Ser. No. 07/633,190 filed Dec. 28, 1990, now U.S. Pat. No. 5,053,052, which is a continuation of application Ser. No. 07/406,269 filed Sep. 12, 1990, now abandoned.

The invention relates to 2-substituted paraaminophenols and their use in dye compositions for dyeing keratinous fibres and particularly human hair, these dye compositions being employed for dyeing known as oxidation dyeing or permanent dyeing.

This dyeing process enables hair to be dyed a large number of shades.

The dyeing of keratinous fibres using so-called oxidation dyeing employs oxidation dye precursors, also called oxidation bases, which are colourless, but develop a durable colour in the keratinous fibres in contact with an oxidizing agent. Substituted or unsubstituted para-phenylenediamines, ortho-phenylenediamines, para-aminophenols and ortho-aminophenols are known as oxidation dye precursors. These oxidation dye precursors can be mixed with one or more compounds known as "couplers". These couplers are generally chosen from meta-diamines, meta-aminophenols, meta-diphenols and phenols.

The subject of the invention is new compounds consisting of 2-substituted para-aminophenols of formula (I):

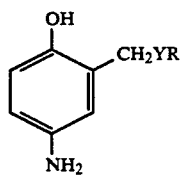

in which Y denotes an oxygen or sulphur atom and R denotes a $C_1$–$C_6$ alkyl, $C_1$–$C_6$ hydroxyalkyl, $C_2$–$C_6$ polyhydroxyalkyl or $C_1$–$C_6$ haloalkyl radical, with the condition that when Y denotes an oxygen atom R is not methyl or ethyl and when Y denotes a sulphur atom R is not ethyl, and their salts.

Another subject of the invention is dye compositions for keratinous fibres and in particular for human hair, containing in an aqueous carrier one or more oxidation dye precursors of formula (I'):

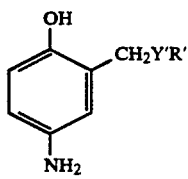

in which Y' denotes an oxygen or sulphur atom and R' denotes a $C_1$–$C_6$ alkyl, $C_1$–$C_6$ hydroxyalkyl, $C_2$–$C_6$ polyhydroxyalkyl or $C_1$–$C_6$ haloalkyl radical; or a salt of one or more compounds of formula (I,). The salts are preferably hydrochlorides or sulphates.

The dye compositions containing one or more compounds of formula (I) make it possible to impart to hair colours which are stable to washing, to light and to inclement weather, by oxidative coupling with other oxidation dye precursors and/or couplers. Furthermore, para-aminophenols of formula (I') have the advantage of a good harmlessness.

The preferred compounds of formula (I') are the following:
4-amino-2-[(β-hydroxyethylthio)methyl]phenol,
4-amino-2-[(methylthio)methyl]phenol,
4-amino-2-methoxymethylphenol (which can be prepared according to the process described in German Patent 148,977),
4-amino-2-ethoxymethylphenol( which can be prepared according to the process described in German Patent 148,977),
4-amino-2-[(β-hydroxyethoxy)methyl]phenol,
4-amino-2-[(β,γ-dihydroxypropylthio)methyl]phenol, and
4-amino-2-[(2',2',2'-trifluoroethoxy)methyl]phenol.

Compounds of formula (I) are prepared in two stages from the substituted nitrophenol of formula (III) in which X denotes a halogen, according to the following reaction scheme:

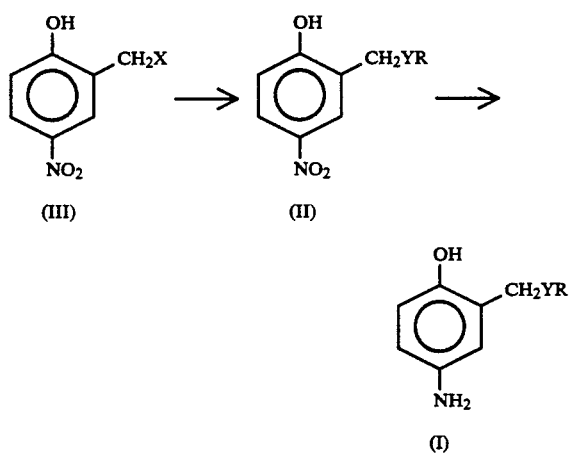

The compound of formula (I) is obtained by reduction of the compound of formula (II) where Y and R have the meanings defined above. Among the traditional methods of reduction there may be mentioned reduction using sodium hydrosulphite in an alkaline medium at a temperature below 80° C, or else a catalytic reduction in a hydroalcoholic medium, under hydrogen pressure, in the presence of a catalyst such as palladium on charcoal or nickel.

The compound of formula (II) can be prepared by reaction with an alcoholate or a thiolate of formula (IV):

$$M\text{—}Y\text{—}R \quad (IV)$$

in which M denotes an alkali metal or alkaline-earth metal and Y and R have the meanings defined above. The alcoholate and the thiolate of formula (IV) can be advantageously prepared in situ according to the reaction scheme:

$$MOH + HYR \rightarrow MYR + H_2O$$

it being possible for the compound HYR to serve also as a solvent.

Among the solvents which can be employed for the preparation of the compounds of formula (II) there may be mentioned, besides the compound HYR, dioxane, N,N-di-methylformamide and N-methylpyrrolidone, which are employed by themselves or mixed. The reaction temperature is usually less than 100° C.

The dye compositions for keratinous fibres and particularly for human hair, according to the invention, contain at least one compound of formula (I') in an aqueous carrier.

Compounds of formula (I') are employed in the compositions of the invention in concentrations of between 0.02 and 6 % and preferably between 0.15 and 5 % by weight, relative to the total weight of the composition.

The compositions of the invention may also contain other oxidation dye precursors.

Among these oxidation dye precursors should be mentioned para-phenylenediamines and para-aminophenols other than those of formula (I'), ortho-phenylenediamines and ortho-aminophenols.

Among the para-phenylenediamines there should be mentioned more particularly:
para-phenylenediamine,
para-tolylenediamine,
2,6-dimethyl-para-phenylenediamine,
2,6-dimethyl-3-methoxy-para-phenylenediamine,
N-(β-methoxyethyl)-para-phenylenediamine,
N-[β-(β'-hydroxyethoxy)ethyl]-4-aminoaniline,
N,N-di(β-hydroxyethyl)-4-aminoaniline,
N,N-(ethyl,carbamylmethyl)-4-aminoaniline,
and their salts.

Among the para-aminophenols there should be mentioned more particularly:
para-aminophenol,
2-methyl-4-aminophenol,
2-chloro-4-aminophenol,
2,6-dimethyl-4-aminophenol,
2,3-dimethyl-4-aminophenol,
2,5-dimethyl-4-aminophenol,
and their salts.

Among the ortho-phenylenediamines and the orthoaminophenols which may be substituted on the nucleus or on the amino functional groups there should be mentioned in particular 1-amino-2-hydroxybenzene, 6-methyl-1-hydroxy- 2-aminobenzene and 4-methyl-1-amino-2-hydroxybenzene.

The dye compositions forming the subject of the present invention generally contain, in combination with the compounds (I') and optionally with para-phenylenediamines or with other para-aminophenols, couplers which, on oxidative coupling with the oxidation bases, yield indoanilines, indamines or indophenols of diverse shades which contribute to modifying and enhancing with highlights the "background" colours imparted to hair by the products of condensation of the oxidation bases with themselves.

Among the couplers there may be mentioned in particular meta-diphenols, meta-aminophenols, meta-phenylenediamines, meta-acylaminophenols, meta-ureidophenols, meta-carbalkoxyaminophenols, α-naphthol, couplers containing an active methylene group, such as β-ketonic compounds and pyrazolones.

Among meta-diphenols there may be mentioned:
resorcinol,
2-methylresorcinol,
5-methylresorcinol,
2,4-dihydroxyphenoxyethanol,
resorcinol monomethyl ether, and
2,4-dihydroxyanisole.

Among meta-aminophenols there may be mentioned:
meta-aminophenol,
2-methyl-5-aminophenol,
2-methyl-N-(β-hydroxyethyl)-5-aminophenol,
2-methyl-N-(β-mesylaminoethyl)-5-aminophenol,
2,6-dimethyl-3-aminophenol,
6-hydroxybenzomorpholine,
and their salts.

Among meta-phenylenediamines there may be mentioned:
meta-phenylenediamine,
2,4-diaminophenoxyethanol,
2,4-dimethoxy-1,3-diaminobenzene,
1,3,5-trimethoxy-2,4-diaminobenzene,
2,4-diaminoanisole,
6-aminobenzomorpholine,
[2-N-(β-hydroxyethyl)amino-4-amino]phenoxyethanol,
[4-N-(β-hydroxyethyl)amino-2-amino]phenoxyethanol,
2-amino-4-N-(β-hydroxyethyl)aminoanisole,
4,5-di(β-hydroxyethoxy)-1,3-diaminobenzene,
1-β-hydroxyethoxy-2,4-diaminobenzene,
and their salts Among the other couplers which can be employed in the dye compositions of the invention there should be mentioned more particularly:
3,4-methylenedioxyphenol,
3,4-methylenedioxyaniline,
2-bromo-4,5-methylenedioxyphenol,
2-chloro-4,5-methylenedioxyphenol, and
2-methoxy-4,5-methylenedioxyaniline.

The total weight of the oxidation dye precursors and of the couplers employed in the dye compositions according to the invention is preferably from 0.15 to 7 % by weight of the total weight of the dye composition.

The dye compositions according to the invention may also contain direct dyes such as azo or anthraquinone dyes and the nitro derivatives of the benzene series, which allow the colours contributed by the oxidation dye precursors and/or the couplers to be tinted or enhanced with highlights.

The pH of the dye composition is generally between 8 and 11 and preferably between 9 and 11. This pH is adjusted to the desired value with the aid of an alkalifying agent such as aqueous ammonia, alkali metal carbonates or alkanolamines, such as mono-, di- or triethanolamine.

In their preferred embodiment, the dye compositions in accordance with the invention contain anionic, cationic, nonionic or amphoteric surface-active agents or mixtures thereof. These surface-active agents are present in the compositions in accordance with the invention in proportions of between 0.5 and 40 % by weight, and preferably between 2 and 30 % by weight, relative to the total weight of the composition.

These compositions may also contain organic solvents to dissolve the compounds which might not be sufficiently soluble in water. Among these solvents there may be mentioned by way of example $C_1$-$C_8$ alcohols such as ethanol, isopropanol, benzyl alcohol and phenylethyl alcohol, glycerol, glycols or glycol ethers such as 2-butoxyethanol, ethylene glycol, propylene glycol, diethylene glycol monoethyl ether and monomethyl ether, and similar compounds and mixtures thereof. The solvents are preferably present in a proportion of between 1 and 40 % by weight, and in particular between 2 and 30 % by weight, relative to the total weight of the composition.

The thickening agents which may be added to the compositions in accordance with the invention are taken especially from the group consisting of sodium alginate, gum arabic, cellulose derivatives such as methyl cellulose, hydroxyethyl cellulose, hydroxypropyl cellulose, hydroxymethyl cellulose and carboxymethyl cellulose, acrylic acid polymers and xanthan gum. It is also possible to employ inorganic thickening agents such as bentonite. These thickening agents are preferably present in proportions of between 0.1 and 5 % by weight, and in particular between 0.5 and 3 % by weight of the total weight of the composition.

The compositions may contain antioxidants chosen in particular from sodium sulphite, thioglycolic acid, sodium bisulphite, ascorbic acid and hydroquinone. These antioxidants are present in the composition in proportions of between 0.05 and 1.5 % by weight of the total weight of the composition.

Other adjuvants which can be employed in accordance with the invention are, for example, penetrating agents, sequestering agents, buffers and perfumes.

The dye compositions in accordance with the invention may be presented in various forms such as in the form of liquids, creams, gels or any other suitable form for producing dyeing of keratinous fibres and especially of human hair. They may also be packaged in aerosol bottles in the presence of a propellent agent.

The dye compositions according to the invention are employed in a process for dyeing hair employing development by means of an oxidizing agent.

In accordance with this process, the dye composition described above is mixed with an oxidizing solution at the time of use, in a sufficient quantity to oxidize the oxidation dye precursors, and the mixture obtained is then applied to hair.

The oxidizing solution contains, in aqueous solution, oxidizing agents chosen from the group consisting of hydrogen peroxide, urea peroxide and persalts, such as ammonium persulphate. A solution of hydrogen peroxide at a concentration of 6 % by weight (20 volumes) is preferably employed.

According to the dyeing process generally employed, the mixture obtained is applied to hair at ambient temperature or at a temperature not exceeding 40° C, is left in place for 10 to 40 minutes and preferably for 15 to 30 minutes, after which the hair is rinsed, is washed with a shampoo, is rinsed again and is dried.

Another process for making use of the oxidation dye precursor of formula (I'), in accordance with the ivention, consists in dyeing hair by following a process in several steps, according to which, in a first step, the oxidation dye precursor of a para type is applied by means of a composition as defined above and, in a second step, the coupler(s) is (are) applied. The oxidizing agent is present in the composition applied in the second step or else applied to the hair itself in a third step, the conditions of application, of washing and of drying being identical with those shown for the single-stage process described above.

The invention is illustrated by the examples which follow.

Examples of Preparation

EXAMPLE 1

Preparation of 4-amino-2-[(β-hydroxyethylthio)methylphenol

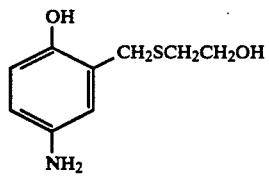

0.085 moles (19.5 g) of 4-nitro-2-[(β-hydroxyethylthio)methyl]phenol are added to a solution of 16 g of sodium hydroxide (NaOH) pellets in 135 ml of water, followed portionwise, so as to maintain the temperature between 70° C. and 75° C., by 55 g of sodium hydrosulphite. After the end of addition stirring is continued for 20 minutes at 75° C. After cooling, the expected product is precipitated by neutralizing the reaction mixture with acetic acid. After filtering off, followed by washing with water and drying, the product obtained is recrystallized from acetonitrile. It melts at 121° C.

Analysis of the product obtained gives the following results:

| | Calculated for $C_9H_{13}NO_2S$ | | | | |
| --- | --- | --- | --- | --- | --- |
| | C | H | N | O | S |
| Analysis | 54.24 | 6.58 | 7.03 | 16.06 | 16.09 |
| Found | 54.02 | 6.62 | 7.00 | 16.17 | 15.92 |

EXAMPLE 2

Preparation of 4-amino-2-[(methylthio)methyl]phenol

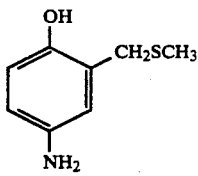

0.085 moles (17 g) of 4-nitro-2-[(methylthio)methyl]phenol are added to a solution of 16 g of sodium hydroxide (NaOH) pellets in 135 ml of water, followed portionwise, so as to maintain the temperature between 70° C. and 75° C., by 55 g of sodium hydrosulphite. After the end of addition stirring is continued for 30 minutes at 75° C. After cooling, the expected product is obtained by neutralizing the reaction mixture with acetic acid. After filtering off, followed by washing with water and drying, it is recrystallized from 96° ethanol. It melts at 166° C. Analysis of the product obtained gives the following results:

| | Calculated for $C_8H_{11}NOS$ | | | | |
| --- | --- | --- | --- | --- | --- |
| | C | H | N | O | S |
| Analysis | 56.79 | 6.55 | 8.28 | 9.45 | 18.91 |
| Found | 56.69 | 6.49 | 8.25 | 9.56 | 18.76 |

EXAMPLE 3

Preparation of 4-amino-2-[(β-hydroxyethoxy)methyl phenol hydrate

1ST STAGE

Preparation of 2-[(β-hydroxyethoxy)methyl]-4-nitrophenol 6.5 moles (93.8 g) of 2-hydroxy-5-nitrobenzyl chloride are heated for 4 hours in 150 ml of ethylene glycol on a boiling water bath. The expected product crystallizes after dilution of the reaction mixture with a liter of iced water. After filtering off followed by drying at 40° C. under air vacuum the product obtained is recrystallized from isopropyl acetate. It melts at 132° C.

Analysis of the product obtained gives the following results:

|  | Calculated for $C_9H_{11}NO_5$ | | | |
| --- | --- | --- | --- | --- |
|  | C | H | N | O |
| Analysis | 50.71 | 5.20 | 6.57 | 37.52 |
| Found | 50.77 | 5.21 | 6.48 | 37.77 |

2ND STAGE

Preparation of 4-amino-2-(β-hydroxyethoxy)methyl]phenol hydrate 25 g of finely powdered zinc and 0.5 g of ammonium chloride are heated under reflux with stirring in 10 ml of water and 50 ml of 96° ethanol. 0.05 moles (10.6 g) of 2-[(β-hydroxyethoxy)methyl]-4-nitrophenol prepared in the preceding stage are added portionwise; after the end of addition the heating is continued for 10 minutes. The zinc is filtered off at boiling temperature. The filtrate is evaporated to dryness, is diluted with ethyl acetate and is then purified by a pass through a silica column (eluent: 40 ethyl acetate/60 cyclohexane). The product obtained is recrystallized from acetonitrile. It melts at 57° C.

Analysis of the product gives the following results:

|  | Calculated for $C_9H_{15}NO_4$ | | |
| --- | --- | --- | --- |
|  | C | H | N |
| Analysis | 53.72 | 7.51 | 6.96 |
| Found | 53.84 | 7.23 | 7.01 |

EXAMPLE 4

Preparation of 4-amino-2-(β,γ-dihydroxypropylthio)methyl]phenol

1ST STAGE

Preparation of 2-[(β,γ-dihydroxypropylthio)methyl]-4-nitrophenol 13.2 g of potassium hydroxide pellets (85 %) are heated to 45° C. in 27 g of thioglycerol. 10 ml of N-methylpyrrolidone are added followed portionwise over 30 minutes by 0.1 mole (23.2 g) of 2-hydroxy-5-nitrobenzyl bromide. The temperature of 67°-70° C. which is obtained is maintained for 30 minutes after the end of addition. The reaction mixture is diluted with 300 g of iced water. After neutralizing with acetic acid, the expected product precipitates. After filtering off, followed by drying at 45° C. under vacuum the product obtained is recrystallized from isopropyl acetate. It melts at 130° C.

Analysis of the product obtained gives the following results:

|  | Calculated for $C_{10}H_{13}NO_5S$ | | | | |
| --- | --- | --- | --- | --- | --- |
|  | C | H | N | O | S |
| Analysis | 46.32 | 5.05 | 5.40 | 30.85 | 12.37 |
| Found | 46.29 | 5.07 | 5.44 | 30.84 | 12.25 |

2ND STAGE

Preparation of 4-amino-2-(β,γ-dihydroxypropylthio)methyl]phenol 0.05 moles (13 g) of 2-[(β,γ-dihydroxypropylthio)methyl]-4-nitrophenol are added to a solution of 8 g of sodium hydroxide pellets in 70 ml of water, followed portionwise, so as to maintain the temperature between 70 and 75° C., by 28 g of sodium hydrosulphite. After the end of addition stirring is continued for 1 hour at 75° C. After neutralization of the reaction mixture with acetic acid the expected product is extracted with ethyl acetate. It is purified by chromatography on a silica column (eluent: ethyl acetate). After recrystallization from acetonitrile it melts at 90° C.

Analysis of the product obtained gives the following results:

|  | Calculated for $C_{10}H_{15}NO_3S$ | | | | |
| --- | --- | --- | --- | --- | --- |
|  | C | H | N | O | S |
| Analysis | 52.38 | 6.59 | 6.11 | 20.93 | 13.98 |
| Found | 52.36 | 6.57 | 6.01 | 21.07 | 13.90 |

EXAMPLE 5

Preparation of 4-amino-2-(2',2',2'-trifluoroethoxy)methyl]phenol

1ST STAGE

Preparation of 4-nitro-2-(2',2',2'-tririfluoroethoxy)methyl]phenol 13.2 g of potassium hydroxide pellets (85 %) and 0.25 moles (25 g) of 2',2',2'-tririfluoroethanol are mixed in 10 ml of N-methylpyrrolidone at 65° C. 0.1 mole (23.2 g) of 2-hydroxy-5-nitrobenzyl bromide is added portionwise over 30 minutes. After the end of addition the temperature is maintained at 85° C. for 1 hour. The reaction mixture is diluted with 300 g of iced water. After neutralization with acetic acid, the expected product separates out. It is purified on a silica column (eluent: 20/80 ethyl acetate/cyclohexane). The product obtained crystallizes slowly. It melts at 60° C.

Analysis of the product obtained gives the following results:

|  | Calculated for $C_9H_8NO_4F_3$ | | | |
| --- | --- | --- | --- | --- |
|  | C | H | N | F |
| Analysis | 43.04 | 3.21 | 5.58 | 22.69 |
| Found | 43.20 | 3.13 | 5.50 | 22.65 |

2ND STAGE

Preparation of
4-amino-2-[(2′,2′,2′-tririfluoroethoxy)methyl]phenol 10 g of zinc powder and 0.2 g of ammonium chloride are heated for 30 minutes under reflux in 20 ml of ethanol and 4 ml of water. 5 g of 4-nitro-2-[(2′,2′,2′-trifluoroethoxy)methyl]phenol (0.02 moles) are added portionwise. After the end of addition heating is continued for 30 minutes. The zinc is removed by filtration at boiling temperature. The expected product is obtained by evaporation of the filtrate under vacuum. Recrystallized from a cyclohexane/ethyl acetate mixture, it melts at 113° C.

Analysis of the product obtained gives the following results:

|  | Calculated for $C_9H_{10}NO_2F_3$ | | | |
| --- | --- | --- | --- | --- |
|  | C | H | N | F |
| Analysis | 48.87 | 4.56 | 6.33 | 25.77 |
| Found | 48.83 | 4.60 | 6.23 | 25.68 |

Examples of Application

EXAMPLE A1

The following dye mixture is prepared:

| | |
| --- | --- |
| 4-Amino-2-methoxymethylphenol | 0.383 g |
| 4-[(β-Hydroxyethyl)amino]-2-hydroxytoluene | 0.417 g |
| Oleyl alcohol polyglycerolated with 2 moles of glycerol | 4.5 g |
| Oleyl alcohol polyglycerolated with 4 moles of glycerol | 4.5 g |
| Oleylamine oxyethylenated with 12 moles of ethylene oxide, sold by Armour Hess Chemical Ltd under the name Ethomeen O 12 | 4.5 g |
| Coprah diethanolamide sold by Henkel under the name Comperlan KD | 9.0 g |
| Propylene glycol | 4.0 g |
| 2-Butoxyethanol | 8.0 g |
| 96° Ethanol | 6.0 g |
| Pentasodium salt of diethylenetriaminepentaacetic acid, sold by Protex under the name Masquol DTPA | 2.0 g |
| Hydroquinone | 0.15 g |
| 35° Bé sodium bisulphite solution | 1.3 g |
| 22° Bé aqueous ammonia | 10.0 g |
| Water q.s. | 100.0 g |
| pH = 10 | |

100 g of 20-volume (6% by weight) hydrogen peroxide are added at the time of use. The mixture, applied for 20 minutes at 35° C. to bleached hair gives it an orangy colour after shampooing and rinsing.

EXAMPLE A2

The following dye mixture is prepared:

| | |
| --- | --- |
| 4-Amino-2-[(methylthio)methyl]phenol | 0.423 g |
| 4-[(β-Hydroxyethyl)amino]-2-hydroxytoluene | 0.417 g |
| Oleyl alcohol polyglycerolated with 2 moles of glycerol | 4.5 g |
| Oleyl alcohol polyglycerolated with 4 moles of glycerol | 4.5 g |
| Oleylamine oxyethylenated with 12 moles of ethylene oxide, sold by Armour Hess Chemical Ltd under the name Ethomeen O 12 | 4.5 g |
| Coprah diethanolamide sold by Henkel under the name Comperlan KD | 9.0 g |
| Propylene glycol | 4.0 g |
| 2-Butoxyethanol | 8.0 g |
| 96° Ethanol | 6.0 g |
| Pentasodium salt of diethylenetriaminepentaacetic acid, sold by Protex under the name Masquol DTPA | 2.0 g |
| Hydroquinone | 0.15 g |
| 35° Bé sodium bisulphite solution | 1.3 g |
| 22° Bé aqueous ammonia | 10.0 g |
| Water q.s. | 100.0 g |
| pH = 10 | |

100 g of 20-volume (6% by weight) hydrogen peroxide are added at the time of use. The mixture, applied for 20 minutes at 35° C. to bleached hair, gives it a light orangy-brown colour after shampooing and rinsing.

EXAMPLE A3

The following dye mixture is prepared:

| | |
| --- | --- |
| 4-Amino-2-methoxymethylphenol | 0.383 g |
| (2,4-Diaminophenoxy)ethanol dihydrochloride | 0.602 g |
| Oleyl alcohol polyglycerolated with 2 moles of glycerol | 4.5 g |
| Oleyl alcohol polyglycerolated with 4 moles of glycerol | 4.5 g |
| Oleylamine oxyethylenated with 12 moles of ethylene oxide, sold by Armour Hess Chemical Ltd under the name Ethomeen O 12 | 4.5 g |
| Coprah diethanolamide sold by Henkel under the name Comperlan KD | 9.0 g |
| Propylene glycol | 4.0 g |
| 2-Butoxyethanol | 8.0 g |
| 96° Ethanol | 6.0 g |
| Pentasodium salt of diethylenetriaminepentaacetic acid, sold by Protex under the name Masquol DTPA | 2.0 g |
| Hydroquinone | 0.15 g |
| 35° Bé sodium bisulphite solution | 1.3 g |
| 22° Bé aqueous ammonia | 10.0 g |
| Water q.s. | 100.0 g |
| pH = 10 | |

100 g of 20-volume (6% by weight) hydrogen peroxide are added at the time of use. The mixture, applied for 20 minutes at 35° C. to 90% naturally white hair, gives it a red-brown colour after shampooing and rinsing.

EXAMPLE A4

The following dye mixture is prepared:

| | |
| --- | --- |
| 4-Amino-2-[(methylthio)methyl]phenol | 0.423 g |
| (2,4-Diaminophenoxy)ethanol dihydrochloride | 0.602 g |
| Oleyl alcohol polyglycerolated with 2 moles of glycerol | 4.5 g |
| Oleyl alcohol polyglycerolated with 4 moles of glycerol | 4.5 g |
| Oleylamine oxyethylenated with 12 moles of ethylene oxide, sold by Armour Hess Chemical Ltd under the name Ethomeen O 12 | 4.5 g |
| Coprah diethanolamide sold by Henkel under the name Comperlan KD | 9.0 g |
| Propylene glycol | 4.0 g |
| 2-Butoxyethanol | 8.0 g |
| 96° Ethanol | 6.0 g |
| Pentasodium salt of diethylenetriaminepentaacetic acid, sold by Protex under the name Masquol DTPA | 2.0 g |
| Hydroquinone | 0.15 g |
| 35° Bé sodium bisulphite solution | 1.3 g |
| 22° Bé aqueous ammonia | 10.0 g |
| Water q.s. | 100.0 g |
| pH = 10 | |

100 g of 20-volume (6% by weight) hydrogen peroxide are added at the time of use. The mixture, applied for 20 minutes at 35° C. to 90% naturally white hair, gives it a grey-red colour after shampooing and rinsing.

EXAMPLE A5

The following dye mixture is prepared:

| | |
|---|---|
| 4-Amino-2-[(β-hydroxyethylthio)methyl]phenol | 0.99 g |
| 4-Amino-2-hydroxytoluene | 0.62 g |
| Oleyl alcohol polyglycerolated with 2 moles of glycerol | 4.5 g |
| Oleyl alcohol polyglycerolated with 4 moles of glycerol | 4.5 g |
| Oleylamine oxyethylenated with 12 moles of ethylene oxide, sold by Armour Hess Chemical Ltd under the name Ethomeen O 12 | 4.5 g |
| Coprah diethanolamide sold by Henkel under the name Comperlan KD | 9.0 g |
| Propylene glycol | 4.0 g |
| 2-Butoxyethanol | 8.0 g |
| 96° Ethanol | 6.0 g |
| Pentasodium salt of diethylenetriamine-pentaacetic acid, sold by Protex under the name Masquol DTPA | 2.0 g |
| Hydroquinone | 0.15 g |
| 35° Bé sodium bisulphite solution | 1.3 g |
| 22° Bé aqueous ammonia | 10.0 g |
| Water q.s. | 100.0 g |
| pH = 10 | |

100 g of 20-volume (6% by weight) hydrogen peroxide are added at the time of use. The mixture, applied for 20 minutes at 35° C. to 90% naturally white hair, gives it a golden orange colour after shampooing and rinsing.

EXAMPLE A6

The following dye mixture is prepared:

| | |
|---|---|
| 4-Amino-2-methoxymethylphenol | 0.215 g |
| para-Phenylenediamine | 0.199 g |
| Resorcinol | 0.197 g |
| meta-Aminophenol | 0.272 g |
| 2-Butoxyethanol | 10.0 g |
| Nonylphenol oxyethylenated with 4 moles of ethylene oxide, sold by Rhône-Poulenc under the name Cemulsol NP 4 | 12.0 g |
| Nonylphenol oxyethylenated with 9 moles of ethylene oxide, sold by Rhône-Poulenc under the name Cemulsol NP 9 | 15.0 g |
| Oleyl alcohol polyglycerolated with 2 moles of glycerol | 1.5 g |
| Oleyl alcohol polyglycerolated with 4 moles of glycerol | 1.5 g |
| Propylene glycol | 6.0 g |
| Ethylenediaminetetraacetic acid sold under the name Trilon B | 0.12 g |
| 22° Bé aqueous ammonia | 11.0 g |
| Thioglycolic acid | 0.6 g |
| Water q.s. | 100.0 g |
| pH = 10.3 | |

100 g of 20-volume (6% by weight) hydrogen peroxide are added at the time of use. The mixture, applied for 20 minutes at 35° C. to 90% naturally white hair, gives it a chestnut colour after shampooing and rinsing.

EXAMPLE A7

The following dye mixture is prepared:

| | |
|---|---|
| 4-Amino-2-[(methylthio)methyl]phenol | 0.177 g |
| 4-(β-Methoxyethyl)aminoaniline dihydrochloride | 1.177 g |
| 4-Methylaminophenol hydrochloride | 0.407 g |
| meta-Aminophenol | 0.195 g |
| 1,3-Diamino-2,4-dimethoxybenzene dihydrochloride | 0.085 g |
| Resorcinol | 0.385 g |
| 6-Hydroxybenzomorpholine | 0.074 g |
| 2-Butoxyethanol | 10.0 g |
| Cetylstearyl alcohol sold by Condea under the name Alfol C 16/18 | 8.0 g |
| Sodium cetylstearyl sulphate sold by Henkel under the name Cire de Lanette E | 0.5 g |
| Ethoxylated castor oil sold by Rhône-Poulenc under the name Cemulsol B | 1.0 g |
| Oleyldiethanolamide | 1.5 g |
| Pentasodium salt of diethylenetriamine-pentaacetic acid sold by Protex under the name Masquol DTPA | 2.5 g |
| 22° Bé aqueous ammonia | 11.0 g |
| Water q.s. | 100.0 g |
| pH = 10.2 | |

100 g of 20-volume (6% by weight) hydrogen peroxide are added at the time of use. The mixture, applied for 20 minutes at 35° C. to bleached hair, gives it an ashen bronze colour after shampooing and rinsing.

EXAMPLE A8

The following dye mixture is prepared:

| | |
|---|---|
| 4-Amino-2-ethoxymethylphenol | 0.84 g |
| 4-Amino-2-hydroxytoluene | 0.62 g |
| 2-Butoxyethanol | 10.0 g |
| Cetylstearyl alcohol sold by Condea under the name Alfol C 16/18 | 8.0 g |
| Sodium cetylstearyl sulphate sold by Henkel under the name Cire de Lanette E | 0.5 g |
| Ethoxylated castor oil sold by Rhône-Poulenc under the name Cemulsol B | 1.0 g |
| Oleyldiethanolamide | 1.5 g |
| Pentasodium salt of diethylenetriamine-pentaacetic acid sold by Protex under the name Masquol DTP | 2.5 g |
| 22° Bé aqueous ammonia | 11.0 g |
| Water q.s. | 100.0 g |
| pH = 10.8 | |

100 g of 20-volume hydrogen peroxide are added at the time of use. The mixture, applied for 20 minutes at 30° C. to 90% naturally white hair, gives it an orangy colour after shampooing and rinsing.

EXAMPLE A9

The following dye mixture is prepared:

| | |
|---|---|
| 4-Amino-2-[(β-hydroxyethoxy)methyl]phenol | 0.451 g |
| 4-[(β-Hydroxyethyl)amino]-2-hydroxytoluene | 0.417 g |
| Nonylphenol oxyethylenated with 4 moles of ethylene oxide, sold by Rhône-Poulenc under the name Cemulsol NP 4 | 12.0 g |
| Nonylphenol oxyethylenated with 9 moles of ethylene oxide, sold by Rhône-Poulenc under the name Cemulsol NP 9 | 15.0 g |
| Oleyl alcohol polyglycerolated with 2 moles of glycerol | 1.5 g |
| Oleyl alcohol polyglycerolated with 4 moles of glycerol | 1.5 g |
| Propylene glycol | 6.0 g |
| Ethylenediaminetetraacetic acid sold under the name Trilon B | 0.12 g |
| 22° Bé aqueous ammonia | 11.0 g |
| Water q.s. | 100.0 g |
| pH = 10.15 | |

90 g of 20-volume hydrogen peroxide are added at the time of use. The mixture, applied for 25 minutes at 30° C. to bleached hair, gives it a bright orange colour after shampooing and rinsing.

EXAMPLE A10

The following dye mixture is prepared:

| | |
|---|---|
| 4-Amino-2-[(β,γ-dihydroxypropylthio)methyl]-phenol | 0.286 g |
| (2,4-Diaminophenoxy)ethanol dihydrochloride | 0.301 g |
| Cetylstearyl alcohol sold by Condea under the name Alfol C 16/18 | 19.0 g |
| 2-Octyldodecanol sold by Henkel under the name Eutanol G | 4.5 g |
| Cetylstearyl alcohol containing 15 moles of ethylene oxide, sold by Henkel under the name Mergital C.S. | 2.5 g |
| Ammonium lauryl sulphate | 10.0 g |
| Cationic polymer containing the following repeat unit: | 4 g |

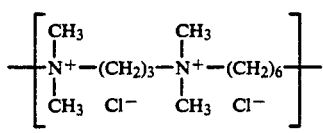

| | |
|---|---|
| Benzyl alcohol | 2.0 g |
| 22° Bé aqueous ammonia | 11 ml |
| Ethylenediaminetetraacetic acid sold under the name Trilon B | 1.0 g |
| 35° Bé sodium bisulphite solution | 1.2 g |
| Water q.s. | 100.0 g |
| pH = 10 | |

100 g of 20-volume hydrogen peroxide are added at the time of use. The mixture, applied for 20 minutes at 30° C. to bleached hair, gives it a grey plum colour after shampooing and rinsing.

EXAMPLE A11

The following dye mixture is prepared:

| | |
|---|---|
| 4-Amino-2-[(β-hydroxyethoxy)methyl]phenol hydrate | 1.3 g |
| p-Phenylenediamine | 0.2 g |
| (2,4-Diaminophenoxy)ethanol dihydrochloride | 0.05 g |
| 2-Trifluoroethoxy-4,5-methylenedioxyaniline | 0.05 g |
| Hydroxyethyl cellulose sold by Union Carbide under the name Cellosize WP 03 | 2.0 g |
| Ammonium lauryl sulphate | 5.0 g |
| 2-Butoxyethanol | 15.0 g |
| 96° Ethanol | 6.0 g |
| 22° Bé aqueous ammonia | 10.0 g |
| 35° Bé sodium bisulphite solution | 1.5 g |
| Hydroquinone | 0.15 g |
| Water q.s. | 100.0 g |
| pH = 10.2 | |

100 g of 20-volume hydrogen peroxide are added at the time of use. The mixture, applied for 25 minutes at 30° C. to 90% naturally white hair, gives it an ashen beige grey colour after shampooing and rinsing.

EXAMPLE A12

The following dye mixture is prepared:

| | |
|---|---|
| 4-Amino-2-ethoxymethylphenol | 1.04 g |
| 4-[(β-Hydroxyethyl)amino]-2-hydroxytoluene | 0.5 g |
| meta-Aminophenol | 0.227 g |
| 2-Bromo-4,5-methylenedioxyphenol | 0.057 g |
| 4-Acetoxy-2-hydroxyaniline hydrochloride | 0.503 g |
| 2-Butoxyethanol | 10.0 g |
| Nonylphenol oxyethylenated, with 4 moles of ethylene oxide, sold by Rhône-Poulenc under the name Cemulsol NP 4 | 12.0 g |
| Nonylphenol oxyethylenated with 9 moles of ethylene oxide, sold by Rhône-Poulenc under the name Cemulsol NP 9 | 15.0 g |
| Oleyl alcohol polyglycerolated with 2 moles of glycerol | 1.5 g |
| Oleyl alcohol polyglycerolated with 4 moles of glycerol | 1.5 g |
| Propylene glycol | 6.0 g |
| Ethylenediaminetetraacetic acid sold under the name Trilon B | 0.12 g |
| 22° Bé aqueous ammonia | 11.0 g |
| Thioglycolic acid | 0.6 g |
| Water q.s. | 100.0 g |
| pH = 9.7 | |

80 g of 20-volume hydrogen peroxide are added at the time of use. The mixture, applied for 27 minutes at 30° C. to 90% naturally white hair, gives it an old rose colour, after shampooing and rinsing.

EXAMPLE A13

The following dye mixture is prepared:

| | |
|---|---|
| 4-Amino-2-[(2',2',2'-trifluoroethoxy)methyl]-phenol | 0.55 g |
| 2,4-Diaminophenoxyethanol | 0.60 g |
| Cetylstearyl alcohol sold by Condea under the name Alfol C 16/18 | 19.0 g |
| 2-Octyldodecanol sold by Henkel under the name Eutanol G | 4.5 g |
| Cetylstearyl alcohol containing 15 moles of ethylene oxide, sold by Henkel under the name Mergital C.S. | 2.5 g |
| Ammonium lauryl sulphate | 10.0 g |
| Cationic polymer containing the following repeat unit: | 4.0 g |

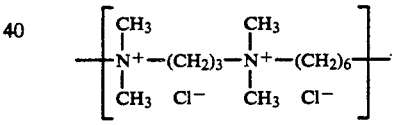

| | |
|---|---|
| Benzyl alcohol | 2.0 g |
| 22° Bé aqueous ammonia | 11 ml |
| Ethylenediaminetetraacetic acid sold under the name Trilon B | 1.0 g |
| 35° Bé sodium bisulphite solution | 1.2 g |
| Water q.s. | 100.0 g |
| pH = 9.4 | |

90 g of 20-volume hydrogen peroxide are added at the time of use. The mixture, applied for 20 minutes at 35° C. to bleached hair, gives it a purple-violet colour after shampooing and rinsing.

EXAMPLE A14

The following dye mixture is prepared:

| | |
|---|---|
| 4-Amino-2-[(2',2',2'-trifluoroethoxy)methyl]-phenol | 0.66 g |
| 2-Methyl-5-aminophenol | 0.369 g |
| Hydroxyethyl cellulose sold by Union Carbide under the name Cellosize WP 03 | 2.0 g |
| Ammonium lauryl sulphate | 5.0 g |
| 2-Butoxyethanol | 15.0 g |
| 96° Ethanol | 6.0 g |
| 22° Bé aqueous ammonia | 10.0 g |
| 35° Bé sodium bisulphite solution | 1.5 g |

| -continued | |
|---|---|
| Hydroquinone | 0.15 g |
| Water q.s. | 100.0 g |
| pH = 10.3 | |

100 g of 20-volume hydrogen peroxide are added at the time of use. The mixture, applied for 25 minutes at 35° C. to bleached hair, gives it an orange colour after shampooing and rinsing.

We claim:

1. A 2-substituted para-aminophenol of formula (I):

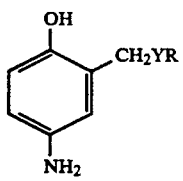
(I)

in which Y denotes an oxygen atom, and R denotes a $C_1$–$C_6$ alkyl, a $C_1$–$C_6$ hydroxylalkyl or a $C_2$–$C_6$ polyhydroxylalkyl radical or a salt thereof; with the condition that R is not methyl or ethyl.

2. A 2-substituted para-aminophenol of formula (I) according to claim 1, wherein R denotes a beta-hydroxyethyl radical.

3. A 2-substituted para-aminophenol of formula (I) according to claim 1, in the form of a hydrochloride or sulfate.

4. A 2-substituted para-aminophenol of formula (I):

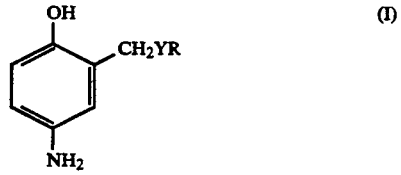
(I)

in which Y denotes a sulphur atom, and R denotes a $C_1$–$C_6$ hydroxyalkyl or a $C_2$–$C_6$ polyhydroxyalkyl radical; or a salt thereof.

5. A 2-substituted para-aminophenol of formula (I) according to claim 4, where R denotes a beta-hydroxyethyl or a beta, gamma-dihydroxypropyl radical.

6. A 2-substituted para-aminophenol of formula (I) according to claim 4, in the form of a hydrochloride or sulfate.

* * * * *